United States Patent [19]

Tsuchihashi et al.

[11] 4,002,682
[45] Jan. 11, 1977

[54] AROMATIC ENAMINOSULFOXIDE DERIVATIVES

[75] Inventors: Genichi Tsuchihashi, Tama; Katsuyuki Ogura, Sagamihara, both of Japan

[73] Assignee: Sagami Chemical Research Center, Tokyo, Japan

[22] Filed: Mar. 6, 1975

[21] Appl. No.: 555,993

Related U.S. Application Data

[62] Division of Ser. No. 396,366, Sept. 12, 1973, Pat. No. 3,898,785.

[30] Foreign Application Priority Data

| Sept. 12, 1972 | Japan | 47-90948 |
| Sept. 12, 1972 | Japan | 47-90949 |
| Sept. 12, 1972 | Japan | 47-90952 |
| Oct. 18, 1972 | Japan | 47-103606 |

[52] U.S. Cl. .................. 260/570.5 S; 260/455 R; 260/490; 260/491; 260/583 EE
[51] Int. Cl.$^2$ .............. C07C 149/42; C07C 149/24
[58] Field of Search ............................ 260/570.5 S

[56] References Cited

FOREIGN PATENTS OR APPLICATIONS 2,345,775  3/1974  Germany ................. 260/570.5 S

OTHER PUBLICATIONS

Ogura et al., J. Am. Chem. Soc., vol. 96(6), 1960–1962 (1974).

*Primary Examiner*—Daniel E. Wyman
*Assistant Examiner*—John J. Doll
*Attorney, Agent, or Firm*—Wenderoth, Lind & Ponack

[57] ABSTRACT

Enaminosulfoxides of the formula,

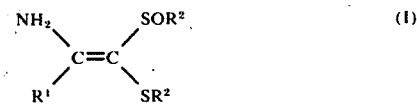

in which $R^1$ is alkyl, dialkoxyalkyl, phenylalkyl, phenyl, halophenyl, alkylphenyl, alkoxyphenyl or dialkoxyphenyl groups, said alkyl and alkoxy each containing 1 to 4 carbon atoms, and each $R^2$ is independently alkyl of 1 to 4 carbon atoms, phenyl, tolyl or chlorophenyl groups, wherein at least one of the $R^1$ and $R^2$ is aromatic. These compounds can be used to synthesize keto acid derivatives and acylamino acid esters which have well known utilities.

10 Claims, No Drawings

AROMATIC ENAMINOSULFOXIDE DERIVATIVES

This is a division of application Ser. No. 396,366, filed Sept. 12, 1973, now U.S. Pat. No. 3,898,785, issued Aug. 5, 1975.

This invention relates to novel enaminosulfoxides, a process for their preparation, and the methods for making various useful chemical compounds from the enaminosulfoxides.

According to the invention, novel enaminosulfoxides of the following general formula (I) are provided.

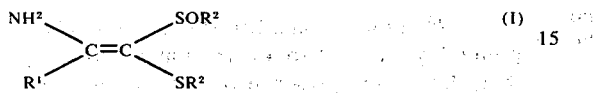

in which $R^1$ is a member of the group consisting of alkyl, dialkoxyalkyl, phenylalkyl, phenyl, halophenyl, alkylphenyl and dialkoxyphenyl groups, said alkyl and alkoxy each containing 1 to 4 carbon atoms, and two $R^2$'s are each independently a member of the group consisting of alkyl of 1 to 4 carbon atoms, tolyl, and halophenyl groups.

The enaminosulfoxides of the above formula (I) are highly valuable because they are easily convertible to various useful compounds. For example, various ketoacid derivatives and acylamino acid esters can be synthesized from the enaminosulfoxides, and so synthesized compounds can be further converted to the corresponding amino acids. Synthesis of such compounds from the enaminosulfoxides will be later described in further details.

The specific groups preferred as $R^1$ of the formula (I) include: methyl, ethyl, i-propyl, butyl, dimethoxypropyl, dimethoxybutyl, benzyl, phenethyl, phenylbutyl, phenyl, chlorophenyl, tolyl, methoxyphenyl, dimethoxyphenyl, and diethoxyphenyl.

Also the specific groups preferred as $R^2$ of the formula (I) include: methyl, ethyl, i-propyl, butyl, tolyl, chlorophenyl, and phenyl.

Thus the typical of the enaminosulfoxides of the formula (I) are as follows:
1-methylsulfinyl-1-methylthio-2-aminopropene,
1-methylsulfinyl-1-methylthio-2-amino-3-methyl-1-butene,
1-methylsulfinyl-1-methylthio-2-amino-2-amino-2-phenylethylene,
1-methylsulfinyl-1-methylthio-2-amino-3-phenylpropene,
1-methylthio-1-(p-tolysulfinyl)-2-amino-2-phenylethylene,
1-(p-chlorophenyl)sulfinyl-1-(p-chlorophenyl)thio-2-amino-5,5-dimethoxy-1-pentene,
1-isopropylsulfinyl-1-isopropylthio-2-amino-5,5-dimethoxy-1-pentene,
1-methylsulfinyl-1-methylthio-2-amino-5,5-dimethoxy-1-pentene,
1-methylsulfinyl-1-methylthio-2-amino-2-(m-tolyl)ethylene,
1-methylsulfinyl-1-(p-tolylthio)-2-amino-2-phenylethylene,
1-methylsulfinyl-1-methylthio-2-amino-4-phenyl-1-butene,
1-methylsulfinyl-1-methylthio-2-amino-2-(p-methoxyphenyl)ethylene,
1-methylsulfinyl-1-methylthio-2-amino-2-(p-chlorophenyl)ethylene.

The invention also provides a method for the preparation of enaminosulfoxides of formula (I). The method comprises reacting a nitrile of the formula (II) below,

in which $R^1$ has the same significance as hereinbefore defined, with a sulfoxide of the formula (III) below,

in which $R^2$'s have the same significance as hereinbefore defined, in the presence of the metalating agent, and contacting the resulting reaction mixture with a protic material to form an enaminosulfoxide of the formula (I).

The nitriles of formula (II) serving as the starting materials are the compounds normally easily available at low costs. Whereas the sulfoxides of formula (III) can be easily formed by the method previously developed by us, i.e., by oxidation of formaldehyde mercaptals or by reacting α-halosulfoxide with thiol. (Refer to U.S. Pat. No. 3,742,066; German Patent Publication No. 2130923).

"Metalation" has been known as the process of attaching a metal atom to a carbon atom of an organic molecule, and the metalating agent is a reagent used in the metalation. The use of a metalating agent in the present invention induces the replacement of one hydrogen atom on the methylene group interposing between the sulfoxide group and sulfide group in the compound of formula (III), with an alkali metal. Suitable metalating agents include, for example, alkali metal hydrides such as sodium hydride and potassium hydride, and organoalkali metal compounds such as methyl lithium, butyl lithium, phenyl lithium, lithium diisopropylamide, and lithium cyclohexylisopropylamide. Of the above-named metalating agents, sodium hydride is the least expensive and easily available, and therefore the most preferred. Approximately equivalent amount of the metalating agent to that of the starting sulfoxide can be used with satisfactory results.

The reaction of the compound of formula (II) with that of formula (III) in the presence of a metalating agent is preferably performed in an organic solvent. The solvent to be employed should be inert to the reaction, or, in other word, aprotic. Examples of such solvent include tetrahydrofuran, dioxane, 1,2-dimethoxyethane, ether, benzene, toluene, dimethylformamide and hexamethylphosphoric triamide.

The reaction temperature is not critical, but normally those of 0° to 100° C. are selected. At the temperatures below 0° C., the rate of reaction becomes low, and at the temperatures exceeding 100° C., side reactions are apt to take place.

The reaction time is variable depending on the types of starting materials, type of the metalating agent, and the reaction temperature employed, but normally it ranges from 1 to 50 hours.

After completion of the above reaction, the reaction mixture is contacted with a protic material, and whereupon the object enaminosulfoxide of formula (I) is obtained in free form. The protic material is linked with the alkali metal ion originating from the metalating agent, to release the hydrogen ion, and whereby the free enaminosulfoxide is formed. Examples of the useful protic material include water; alcohols such as methanol and ethanol; organic carboxylic acids such as acetic acid; aqueous solutions of inorganic acids such as hydrochloric acid and sulfuric acid; and aqueous solutions of ammonium chloride. Of the foregoing protic materials, water is the most easily available, and can sufficiently achieve the purpose. It is satisfactory to use the protic material of the amount equivalent to that of the metalating agent, but the use of excessive protic material produces no detrimental effect.

The reaction mechanism through which the enaminosulfoxide of formula (I) is produced can be expressed by the equations below:

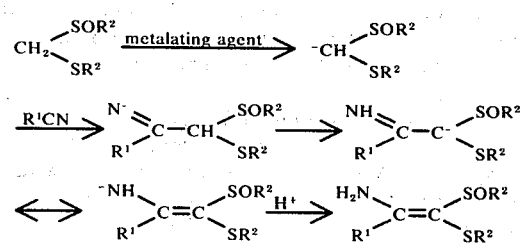

Examples of the above-specified enaminosulfoxides and their preparation are shown in the later-appearing Examples A-1 through A-19.

Now the methods of deriving from the enaminosulfoxides the corresponding α-keto-acid derivatives, α-acylamino-α-[alkyl (or aryl) thio] carboxylic acid thiol esters, acylamino acid esters, α-thioamino acid derivatives, and amino acid derivatives, will be explained by the order stated. In the following explanations, $R^1$'s and $R^2$'s appearing in the chemical formulae have the same definitions as given in the foregoing.

Preparation of α-keto-acid derivatives

Upon subjecting the novel enaminosulfoxides of formula (I) to an acidic hydrolysis, the corresponding α-keto-acid derivatives can be readily formed. The reaction can be illustrated by the equation below:

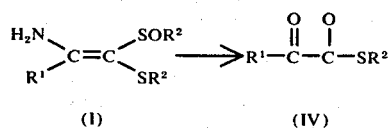

The α-keto-acid derivatives of formula (IV) are a group of novel compound.

The acids to be employed for the acidic hydrolysis include mineral acids, organic acids, and Lewis acids. More specifically, mineral acids such as hydrochloric and sulfuric acids; organic acids such as p-toluenesulfonic acid and acetic acid; and Lewis acids such as cupric chloride and stannic chloride; are preferred. Because the acid acts as the catalyst in said hydrolysis, use thereof in the catalytic amount is satisfactory in cases of mineral acids and organic acids.

The reaction is preferably performed in a solvent which takes no part in the reaction, such as water, tetrahydrofuran, methylene chloride, and the like.

The reaction temperature is not critical. The reaction progresses smoothly at room temperature, not requiring particular heating or cooling, and the object product can be obtained in the high yield.

If the above reaction is performed in the presence of an alcohol ($R^3OH$), the α-keto-acid derivatives of formula (V) are obtained according to the equation below:

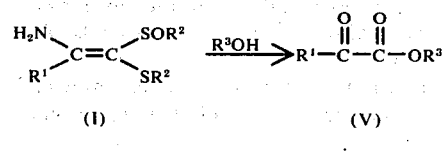

The $R^3$ in the formula $R^3OH$ denotes an alkyl group, preferably that of 1 to 4 carbon atoms. It is presumed that, due to the presence of such an alcohol, the α-keto-acid derivatives of formula (IV) formed upon the acid hydrolysis of enaminosulfoxide of formula (I) further reacts with the alcohol, to be converted to the form of above formula (V).

The α-keto-acid derivatives of the formulae (IV) and (V) are useful as the starting materials of various amino acids or heterocyclic compounds. Upon subjecting those α-keto-acid derivatives to transamination reaction or fermentation process, optically active amino acids can be formed. Or, the amino acid may also be formed by first converting the α-keto-acid derivatives to oxime derivatives and thereafter reducing the same. When the α-keto-acid derivatives are reacted, for example, with o-phenylenediamine, heterocyclic compounds can be obtained.

For the preparation of α-keto-acid, various methods have been known, but the use of nitrile as the starting material is entirely unknown. According to the present invention, a process for converting the enaminosulfoxides of the foregoing formula (I), synthesized from the nitriles as the starting materials, to α-keto-acids is provided. Thus the process for the preparation of α-keto-acids of the invention is novel. Furthermore, industrial advantages gained by this novel process are indeed great, because the nitriles are readily available at low cost.

Examples of the α-keto-acid derivatives of the formulae (IV) and (V), and their preparation are shown in the later-appearing Examples B-1 through B-9.

Preparation of α-acylamino-[α-alkyl (or aryl) thio] carboxylic acid thiol esters Upon reacting the enaminosulfoxides of formula (I) with an acylating agent, the corresponding α-acylamino-[α-alkyl (or aryl) thio] carboxylic acid thiol esters of formula (VI) are produced according to the equation below:

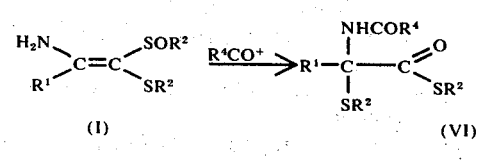

In the above equation, $R^4CO^+$ denotes the acyl group in the acylating agent, and $R^4$ stands for an alkyl or aryl group. Acylating agents have been conventionally employed in acylating reactions in general and are well known. As the typical examples, acid anhydrides such as acetic anhydride, propionic anhydride, etc., and acid chlorides such as benzoyl chloride, acetyl chloride, etc. may be named.

The reaction is carried out optionally in the presence of a solvent as the reaction medium. If the acylating agent to be used is a solid substance, preferably a solvent which dissolves the acylating agent is used as the reaction medium. When a basic substance is caused to be present in the reaction system, it is observed that the substance acts as an acid acceptor and the reaction progresses more smoothly. However, the presence of such a basic substance is not essential. Examples of suitable basic substances include pyridine, and acetates or hydroxides of alkali metals.

The reaction temperature is not critical. Normally special heating or cooling is not required, and the reaction can be performed at room temperature, but when the reaction is violently exothermic depending on the types of starting material, cooling is preferred.

The thiol esters of the formula (VI) are novel. They possess the valuable utility as the materials for amino acids. The corresponding amino acids can be easily formed by subjecting the thiol esters to a desulfurizing treatment.

Exemplary thiol esters of the formula (VI) and their preparation are shown in the later-appearing Examples C-1 through C-11.

Preparation of acylamino acid esters

Acylamino acid esters can be formed by subjecting the thiol esters of formula (VI) to a reducing desulfurization reaction in the presence of an alcohol and activated transition metal catalyst. The mechanism of forming the acylamino acid esters of formula (VII) can be expressed by the equation below:

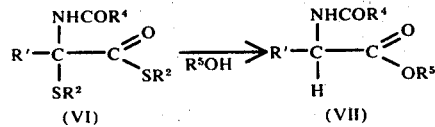

In the above, $R^5OH$ denotes an alcohol, and $R^5$ stands for an alkyl group, preferably a lower alkyl group of 1 to 4 carbon atoms.

The most typical of the activated transition metal catalyst are Raney Ni or Co, and Urushibara Ni, which are well known in the art. For example, Raney Ni (WII) is employed with preference because its preparation and storage are easy. Also Raney Ni (WII) is disclosed in Org. Synth., Coll. Vol. III, 181 (1955).

The above reaction can be performed in the presence of a stoichiometric amount or more of the alcohol, at the temperatures ranging from 0° C. to the boiling point of said alcohol. The reaction, however, normally progresses smoothly at room temperature, without particular heating or cooling.

In the reducing desulfurization reaction is performed in the absence of alcohol but in the presence of a deactivated transition metal (for example, deactivated nickel), the acylamino acid esters of formula (VIII) below can be obtained according to the equation below:

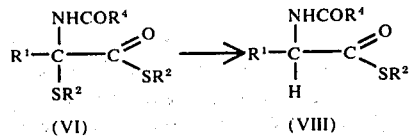

The deactivated nickel suitable for the above usage can be obtained by reducing the activity of Raney Ni or Urushibara Ni. The means for reducing the activity are well known per se. For example, the activated Ni in ethanol may be treated with addition of a minor amount of hydrochloric acid or chloroform, or it may be heated in acetone under reflux. Disclosures on such deactivated Ni can be found, for example, in Chem. Reviews, Vol. 62, 347 (1962).

The reaction is preferably performed in the presence of a suitable medium. As the medium, organic solvents inert to the reaction, such as acetone, alcohol, ether, etc., are used. While the temperature is not a critical factor in the reaction, normally room temperature is employed with advantage.

The acylamino acid esters of both the formulae (VII) and (VIII) can be easily converted to the corresponding amino acids through hydrolysis.

Examples of the acylamino acid esters and methods of their preparation are exemplified in the later-appearing Examples D-1 through D-12.

Preparation of acylamino acids or esters thereof

Upon reacting the thiol ester of formula (VI), wherein $R^1$ represents a non-substituted or substituted alkyl group, with water or alcohol of the formula $R^6OH$ in which $R^6$ stands for hydrogen atom or an alkyl group, preferably a lower alkyl group of 1 to 4 carbon atoms, in the presence of a base, the acylamino acid of formula (IX) or an ester thereof is formed according to the equation below:

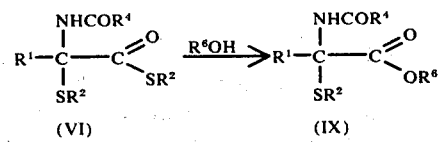

Useful bases in the above reaction include ammonia, organic amines such as diethylamine and triethylamine, and inorganic base such as potassium carbonate and alkali hydroxide. When an inorganic base is used, a salt of the object product tends to be formed, and therefore the reaction system is preferably subjected to a neutralization treatment after the reaction. Because the base acts as a catalyst, it is sufficient to use the same in the catalytic amount, while the inorganic bases are preferably used in excess.

It is satisfactory to use stoichiometric amount of water or alcohol, while it may be used in excess to make it serve both as the reactant and the reaction medium. If desired, organic solvents which are inert to the reaction, such as chloroform, tetrahydrofuran, and the like, may be concurrently used as the reaction medium. The temperature at the time of reaction is not critical, which may be room temperature. The system may be heated to raise the rate of reaction. Normally it is recommended, therefore, that the reaction should be performed at the reflux point of the reaction medium employed.

When the acylamino acid of formula (IX) or an ester thereof is subjected to a reducing desulfurization treatment in the presence of a reducing desulfurizing agent, the amino acid derivatives of formula (X) are formed according to the equation below:

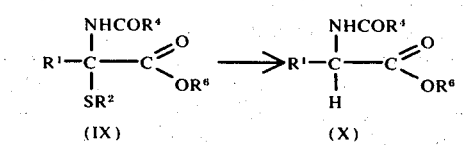

The reducing desulfurizing agent to be employed in the above reaction may be any of those conventionally employed in the reducing desulfurization treatment in general, examples of which including aforesaid activated transition metal catalysts such as Raney nickel and Urushibara nickel, thiolate anions such as methyl mercaptide anion and thiophenolate anion, phosphorous acid esters, phosphorous acid anion, and the like.

The reaction is preferably performed in a solvent, examples of suitable solvents including water, acetone, methylene chloride, alcohol, and ether, etc. The reaction progresses at room temperature, but heating is recommended for increasing the rate of reaction.

When the thiol esters of formula (VI), wherein $R^1$ represents a non-substituted or substituted phenyl group, are reacted with water or alcohol of the aforesaid formula $R^6OH$ is the presence of a base, the amino acid derivatives of formula (X) are directly formed in accordance with the equation below:

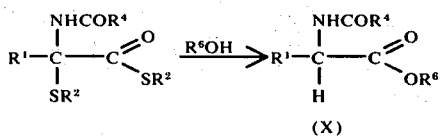

Preferred bases for the above reaction include inorganic bases such as alkali hydroxide and alkali carbonate; and organic bases such as trialkylamine, pyridine, triethylenediamine and tetraalkylammonium hydroxide.

Of the above-named bases, inorganic bases and tetralkylammonium hydroxide tend to give the object product in salt form, and therefore they are preferably used in more than the equivalent amount. If the product is obtained in the form of its salt, it can be neutralized with an acid after the reaction, to be obtained as the desired free acid. If less than the equivalent amount of an organic base is used, in the case of the α-amino-acid derivative of formula (VI), wherein $R^2$ is methyl or ethyl group, the α-thioamino acid derivatives of formula (IX) are apt to be by-produced. In order to avoid such, suitably at least 5 mols of the organic base is used per mol of the starting thiol ester of formula (VI). Using less than 5 mols of the organic base, however, still the object amino acid derivatives of formula (X) can be selectively formed, if the reaction is performed in the concurrent presence of a reducing desulfurization agent such as aforesaid thiol compounds, e.g., thiophenol and alkylmercaptan, or phosphorous acid ester.

If an excessive amount of water or alcohol as the reactant is used, it also acts as the reaction medium. If desired, a substance inert to the reaction, such as chloroform, tetrahydrofuran, and the like, may be used as the reaction medium.

While the reaction progresses smoothly at room temperature, the rate of reaction can be increased by heating. Generally it is preferred to effect the reaction of the reflux temperature of the reaction medium.

The compounds of the formulae (IX) and (X) can be easily converted to the corresponding amino acids through hydrolysis.

Examples of the compounds of formulae (IX) and (X) and methods of their preparation are shown in the later-appearing Examples E-1 through E-24.

EXAMPLE A-1

1.20 Grams of methyl methylthiomethyl sulfoxide was dissolved in 10 ml of tetrahydrofuran (THF), and to which 250 mg of sodium hydride was added under cooling with ice. Then the system was stirred for 30 minutes at room temperature. Subsequently, 1.25 ml of isobutyronitrile was added, followed by 13 hours' stirring at room temperature, further addition of 50 ml of methylene chloride and 1 ml of water, and additional 30 minutes' stirring at room temperature. After drying with Glauber's salt, the reaction mixture was concentrated under reduced pressure to provide a light yellow, crystalline product. Recrystallizing (washing) the same from carbon tetrachloride and cyclohexane, 682 mg of 1-methylsulfinyl-1-methylthio-2-amino-3-methyl-1-butene was obtained as a light yellow solid. The mother liquor was passed through a column chromatography (silica gel, methylene chloride, ethyl acetate, and methanol) to yield 672 mg of a mixture of methyl methylthiomethyl sulfoxide with 1-methylsulfinyl-1-methylthio-2-amino-3-methyl-1-butene as a light yellow oil, which was confirmed to be a mixture of 575 mg of methyl methylthiomethyl sulfoxide and 97 mg of 1-methylsulfinyl-1-methylthio-2-amino-3-methyl-1-butene, upon NMR quantitative analysis. The latter's isolation yield was 41.7%, and the conversion yield was 80.2%. The sample for the analysis was obtained by recrystallizing the product from chloroform-n-hexane.

1-methylsulfinyl-1-methylthio-2-amino-3-methyl-1-butene: m.p. 145°–147° C. (decomposed), colorless crystal.

IR (KBr):
  3410, 3250, 3170, 3010, 1620, 1528, 1000 cm$^{-1}$
NMR (CDCl$_3$):
  δ1.14d (3H, J = 7Hz); 1.25d (3H, J = 7Hz); 3.67 septet (1H, J = 7Hz); 5.33 broad (2H)

| Analyzed as C$_7$H$_{15}$ONS$_2$: | C | H | S |
|---|---|---|---|
| Calculated: | 43.49 | 7.82 | 33.17 |
| Found: | 43.26 | 7.54 | 33.38 |

EXAMPLE A-2

1.78 Grams of methyl methylthiomethyl sulfoxide was dissolved in 20 ml of THF, and to which 375 mg of sodium hydride was added under cooling with ice, followed by 30 minutes' stirring at room temperature. Thereafter 1.6 ml of isobutyronitrile was added and stirred for 16 hours at room temperature and for 6 hours at 50° C., followed by further addition of 70 ml of methylene chloride and 2 ml of water, and subsequent an hour's stirring at room temperature. The reaction mixture was dried with Glauber's salt, and concentrated under reduced pressure to leave a yellow solid. Washing the solid with a carbon tetrachloride-n-hexane system, 1.525 g of 1-methylsulfinyl-1-methylthio-2-amino-3-methyl-1-butene was obtained as a light yellow solid. The washing was concentrated under reduced pressure, and subjected to a column chromatography (silica gel, methylene chloride, ethyl acetate, and methanol) to allow the recovery of 117 mg of methyl methylthiomethyl sulfoxide and 480 mg of 1-methylsulfinyl-1-methylthio-2-amino-3-methyl-1-butene. The isolation yield was 72.3%, and the conversion yield was 77.5%.

EXAMPLE A-3

1.31 Grams of methyl methylthiomethyl sulfoxide was dissolved in 10 ml of THF. To the solution 7 ml of n-butyl lithium solution (15% hexane) was added under cooling with ice, followed by 30 minutes' stirring, addition of 2.0 ml of isobutyronitrile, 1.5 hours' stirring at room temperature, addition of 50 ml of methylene chloride and 3 ml of water, 30 minutes' stirring at room temperature, and finally by the addition of 17 ml of water. The reaction mixture was extracted with methylene chloride (50 ml × 3 times), dried with Glauber's salt, and concentrated under reduced pressure. The concentrate was subjected to a column chromatography (silica gel, methylene chloride, ethyl acetate, and methanol), to allow the recovery of 231 mg of methyl methylthiomethyl sulfoxide and 343 mg of 1-methyl-sulfinyl-1-methylthio-2-amino-3-butyl-1-butene. The yield was 16.9%, and the conversion yield was 20.4%.

EXAMPLE A-4

4.38 Grams of methyl methylthiomethyl sulfoxide was dissolved in 45 ml of THF, and to the solution 900 mg of sodium hydride was added under cooling with ice, and the system was stirred for an hour at room temperature. Upon addition of 4 ml of benzonitrile and subsequent stirring for 42.5 hours at room temperature, the entire system was solidified, to which 100 ml of methylene chloride and 3 ml of water were added, followed by 30 minutes' stirring and then drying with Glauber's salt. The light yellow solid obtained by the subsequent concentration under reduced pressure was washed with 100 ml of carbon tetrachloride, and 5.158 g of 1-methylsulfinyl-1-methylthio-2-amino-2-phenylethylene was obtained as a light yellow solid. The washing was concentrated under reduced pressure, and subjected to a column chromatography (silica gel, ethyl acetate, and methanol) to allow the recovery of 1.106 g of a light yellow, oily substance. Upon NMR analysis, the oily substance was confirmed to be composed of 972 mg of methyl methylthiomethyl sulfoxide and 134 mg of 1-methylsulfinyl-1-methylthio-2-amino-2-phenylethylene. The latter's isolation yield was 66%, and the conversion yield was 84.8%.

The 1-methylsulfinyl-1-methylthio-2-amino-2-phenylethylene was purified by recrystallization from a methylene chloride-carbon tetrachloride system.

1-methylsulfinyl-1-methylthio-2-amino-2-phenylethylene: m.p. 162° – 163° C. (decomposed) light yellow crystals.

IR (KBr):
3360, 3260, 3130, 1617, 1514, 995 cm$^{-1}$

NMR (CDCl$_3$):
δ2.38s (3H); 2.57s (3H); 5.42 broad (2H); 7.38s (5H)

| Analyzed as C$_{10}$H$_{13}$NOS$_2$: | C | H | S |
|---|---|---|---|
| Calculated: | 52.83 | 5.76 | 28.21 |
| Found: | 52.57 | 5.62 | 28.38 |

EXAMPLE A-5

1.830 Grams of methyl methylthiomethyl sulfoxide was dissolved in 20 ml of THF, and to the solution 415 mg of sodium hydride was added under cooling with ice, followed by 90 minutes' stirring at room temperature. Thereafter 1.520 g of benzonitrile was added. The system was stirred for 1.5 hours at room temperature and for 16 hours at 50° C., followed by the addition of 2 ml of water and 70 ml of methylene chloride, and for one hour stirring at room temperature. The reaction mixture was dried with Glauber's salt, and filtrated. The filtrate was concentrated under reduced pressure and the resulting yellow solid was crystallized from ethylene chloride-carbon tetrachloride and a minor amount of cyclohexane. Thus 2.391 g of 1-methylsulfinyl-1-methylthio-2-amino-2-phenylethylene was obtained. The isolation yield was 77.1%.

EXAMPLE A-6

1.753 Grams of methyl methylthiomethyl sulfoxide was dissolved in 20 ml of 1,2-dimethoxyethane, and to the solution 580 mg of potassium hydride was added under cooling with ice, and the system was stirred for one and half hours at room temperature. Upon addition of 1.460g of benzonitrile and subsequent stirring for 15 hours at room temperature and for one hour at 50° C., the system was added with 70 ml of methylene chloride and 2 ml of water, followed by stirring for one hour at room temperature. The mixture was dried with Glauber's salt, and filtrated. The filtrate was concentrated under reduced pressure and the resulting yellow solid was crystallized from methylene chloride-carbon tetrachloride-cyclohexane to obtain 2.208g of 1-methylsulfinyl-1-methylthio-2-amino-2-phenylethylene. The isolation yield was 69%.

EXAMPLE A-7

1.815 Grams of methyl methylthiomethyl sulfoxide was dissolved in 20 ml of dimethylformamide, and the solution was added with 380 mg of sodium hydride under cooling with ice, and then stirred for 1.5 hours at room temperature. Thereafter, upon addition of 1.515g of benzonitrile, the mixture was stirred for 1.5 hours at room temperature and for 10 hours at 50° C., followed by addition of 70 ml of methylene chloride and 2 ml of water and stirring for 20 minutes at room temperature. After drying with Glauber's salt and filtration, the filtrate was concentrated under reduced pressure. The resulting product was crystallized from methylene chloride-carbon tetrachloride-cyclohexane to obtain 2.332 g of 1-methylsulfinyl-1-methylthio-2-amino-2-phenylethylene. The isolation yield was 70%.

EXAMPLE A-8

991 Milligrams of n-butyl lithium was added to 10 ml of a THF solution containing 1.539 g of diisopropylamine to prepare THF solution of lithium diisopropylamide. To this solution 10 ml of THF solution containing 1.890g of methyl methylthiomethyl sulfoxide was added dropwise, followed by stirring 1.5 hours at room temperature. Upon addition of 1.570 g of benzonitrile and stirring for an hour at room temperature and for 18 hours at 50° C., the mixture was added with 70 ml of methylene chloride and 2 ml of water and stirred for an hour at room temperature, followed by drying with Glauber's salt and filtration. The solid obtained by concentration of the filtrate under reduced pressure was crystallized from methylene chloride-carbon tetrachloride-cyclohexane to prepare 2.284g of 1-methylsulfinyl-1-methylthio-2-amino-2-phenylethylene. The isolation yield was 66%.

EXAMPLES A9 – 11

Methyl methylthiomethyl sulfoxide was dissolved in 20 ml of THF, and to the solution sodium hydride was added under cooling with ice, followed stirring 1.5 hours at room temperature. The system was added with various amount of nitrile and then stirred for 1.5 hours at room temperature and for 16 hours at 50° C. Thereafter 70 ml of methylene and 2 ml of water were added to the mixture, followed by stirring for an hour at room temperature. The reaction mixture was dried with Glauber's salt and filtrated. The resulting product was crystallized from methylene chloride-carbon tetrachloride-cyclohexane to recover 1-methylsulfinyl-1-methylthio-2-amino-2-arylethylene.

The reaction conditions and the results are shown in Table below.

| Analyzed as $C_{11}H_{15}NOS_2$: | C | H | S |
|---|---|---|---|
| Found: | 54.80 | 6.18 | 26.39 |

Example A-10: 1-methylsulfinyl-1-methylthio-2-amino-2-(p-chlorophenyl) ethylene
pale yellow crystals: m.p. 150° – 150.5° C. (dec.);
IR (KBr):
3360, 3230, 3080, 1620, 1530, 1000cm$^{-1}$
NMR (CDCl$_3$):
δ2.38s (3H), 2.56s (3H), 5.54 broad (2H), 7.32s (4H)

| Analyzed as $C_{10}H_{12}NOS_2Cl$: | C | H | S |
|---|---|---|---|
| Calculated: | 45.88 | 4.62 | 24.50 |
| Found: | 45.71 | 4.60 | 24.29 |

Example A-11: 1-methylsulfinyl-1-methylthio-2-amino-2-(p-methoxyphenyl) ethylene
colorless crystals: m.p. 156.5° – 157.5° C (dec.);
IR (KBr):
3385, 3230, 3030, 1625, 1605, 1500, 1260, 990, 840cm$^{-1}$
NHR (CDCl$_3$):
δ2.38s (3H), 2.57s (3H), 3.81s (3H), 5.39 broad (2H), 6.87d (2H, J = 9Hz), 7.28d (2H, J = 9Hz).

$$ArCN + CH_3SCH_2SCH_3 \longrightarrow \underset{Ar}{\overset{NH_2}{>}}C=C\underset{SCH_3}{\overset{SOCH_3}{<}}$$

(A)    (B)    (C)

| Ex. | Ar | Amount of compound (A) (g) | Amount of compound (B) (g) | Amount of NaH (mg) | The obtained amount of product (C) (g) | Yield (%) |
|---|---|---|---|---|---|---|
| A-9 | CH$_3$-C$_6$H$_4$- | 1.470 | 1.554 | 330 | 2.058 | 68 |
| A-10 | Cl-C$_6$H$_4$- | 1.801 | 1.623 | 345 | 2.569 | 75 |
| A-11 | MeO-C$_6$H$_4$- | 1.860 | 1.735 | 370 | 2.875 | 80 |

The products obtained in Examples A-9 to A-11 and their properties are as follows:
Example A-9: 1-methylsulfinyl-1-methylthio-2-amino-2-(m-tolyl)ethylene colorless crystals: m.p. 129° – 130° C;
IR (KBr):
3370, 3230, 3095, 1620, 1535, 1005cm$^{-1}$
NMR (CDCl$_3$):
δ2.38s (3H), 2.41s (3H), 2.58s (3H), 5.40 broad (2H), 7.23m (4H).

| Analyzed as $C_{11}H_{15}NOS_2$: | C | H | S |
|---|---|---|---|
| Calculated: | 54.73 | 6.26 | 26.57 |

| Analyzed as $C_{11}H_{15}NO_2S_2$: | C | H | S |
|---|---|---|---|
| Calculated: | 51.33 | 5.88 | 24.92 |
| Found: | 51.39 | 5.92 | 24.88 |

EXAMPLE A-12

2.90 Grams of methyl methylthiomethyl sulfoxide was dissolved in 25 ml of THF, added with 650 mg of sodium hydride under cooling with ice, and stirred for an hour at room temperature. Then 1.8 ml of acetonitrile was added to the system, followed by 12 hours' stirring at room temperature, 4.5 hours' stirring at 50° C., addition of 2 ml of water and 70 ml of methylene chloride, and finally by 2 hours' stirring at room temperature. The reaction mixture was dried with Glauber's salt, concentrated under reduced pressure, and the residue was subjected to a column chromatography (Florisil, methylene chloride, ethyl acetate, and methanol) to allow the recovery of 341 mg of methyl methylthiomethyl sulfoxide and 2.889 g of 1-methylsulfinyl-1-methylthio-2-aminopropene (light yellow crystals). The latter's isolation yield was 75.6%, and the conversion yield was 84.7%.

The analytical sample of the 1-methylsulfinyl-1-methylthio-2-aminopropene was obtained by recrystallization from a methylene chloride-carbon tetrachloride system.

1-Methylsulfinyl-1-methylthio-2-aminopropene: m.p. 114.5° – 115.5° C.

IR (KBr):
3340, 3300 (sh), 3170, 1632, 1550, 1012, 1000cm$^{-1}$

NMR (CDCl$_3$):
$\delta$2.28s (6H), 2.66s (3H), 5.60 broad (2H)

| Analyzed as C$_5$H$_{11}$NOS$_2$: | C | H | S |
|---|---|---|---|
| Calculated: | 36.33 | 6.71 | 38.80 |
| Found: | 36.56 | 6.51 | 38.86 |

EXAMPLE A-13

1.84 Grams of methyl methylthiomethyl sulfoxide was dissolved in 20 ml of THF, added with 800 mg of sodium hydride (as 50% solution) under cooling with ice, and stirred for 30 minutes at room temperature. To the system then 1.8 ml of benzyl cyanide was added, followed by 14 hours' stirring at room temperature, 6 hours' stirring at 60° C., addition of 2 ml of water and 70 ml of methylene chloride, and finally by 2 hours' stirring. The reaction mixture was dried with Glauber's salt, concentrated under a reduced pressure, and the residue was subjected to a column chromatography [silica gel, ethyl acetate-methylene chloride (1:1 mixture), ethyl acetate, and methanol] to allow the recovery of 998 mg of methyl methylthiomethyl sulfoxide and 286 mg of 1-methylsulfinyl-1-methylthio-2-amino-3-phenylpropene. The latter was purified by recrystallization from a chloroform-carbon tetrachloride-n-hexane system. The isolation yield was 8.0%, and the conversion yield was 18.4%.

1-Methylsulfinyl-1-methylthio-2-amino-3-phenylpropene: m.p. 135° – 136° C. (decomposed) light yellow crystals IR (KBr)
3380, 3240, 3160, 3100, 1620, 1536, 1010 cm$^{-1}$ NMR (CDCl$_3$):
$\delta$2.31s (3H), 2.60s (3H), 4.00 broad (2H), 5.40 broad (2H·NH$_2$)

| Analyzed as C$_{11}$H$_{15}$ONS$_2$: | C | H | S |
|---|---|---|---|
| Calculated: | 54.73 | 6.26 | 26.57 |
| Found: | 54.53 | 6.11 | 26.39 |

EXAMPLE A-14

1.316 Grams of methylthiomethyl p-tolyl sulfoxide was dissolved in 10 ml of THF, and to which 175 mg of sodium hydride was added under cooling with ice, followed by an hour's stirring at room temperature. Then 0.9 ml of benzonitrile was added, and the system was stirred for 20 hours at room temperature and for 4 hours at 60° C. After further addition of 50 ml of methylene chloride and 1 ml of water, the reaction mixture was dried with Glauber's salt and concentrated under a reduced pressure. The residue was washed with carbon tetrachloride and n-hexane to give 2.017 g of a light yellow solid, which was dissolved in hot chloroform, and the insoluble matter was filtered. The filtrate was concentrated under a reduced pressure, to leave 1.569 g of 1-methylthio-1-(p-tolylsulfinyl)-2-amino-2-phenylethylene as a light yellow crystals.

The analytical sample was obtained by recrystallizing the above product from a methylene chloride-carbon tetrachloride-n-hexane system.

1-Methylthio-1-(p-tolylsulfinyl)-2-amino-2-phenylethylene: m.p. 145° – 146° C. (decomposed) colorless crystals IR (KBr):
3470, 3225, 3075, 1610, 1520, 1003 cm$^{-1}$ NHR (CDCl$_3$):
$\delta$2.02s (3H), 2.38s (3H), 5.38 broad (2H), 7.17s (5H), 7.47m (4H)

EXAMPLE A-15

3.000 Grams of p-chlorophenyl p-chlorophenylthiomethyl sulfoxide was dissolved in 40 ml of anhydrous THF, and to which 240 mg of sodium hydride was added under cooling with ice, followed by an hour's stirring at 0° C. and another hour's stirring at room temperature. Then 1.29 ml of 4,4-dimethoxybutyronitrile was added dropwise, followed by 18 hours' stirring at room temperature, 24 hours additional stirring at 60° C., addition of 80 ml of methylene chloride and 1 ml of water, and finally by 30 minutes' stirring at 0° C. and 4 hours' stirring at room temperature. The reaction mixture was dried with Glauber's salt, and filtered. Concentrating the filtrate, 3.530 g of a brown oil was obtained, which was passed through a column chromatography (Florisil, methylene chloride, ethyl acetate, and methanol) to yield 595 mg of 1-(p-chlorophenyl)sulfinyl-1-(p-chlorophenyl)thio-2-amino-5,5-dimethoxy-1-pentene. The yield was 14%, and the conversion yield was 25%.

1-(p-Chlorophenyl)sulfinyl-1-(p-chlorophenyl)thio-2-amino-5,5-dimethoxy-1-pentene (recrystallized from a carbon tetrachloride-cyclohexane system): m.p. 103° – 104° C. colorless crystals IR (KBr): 1005, 3183, 3290, 3370 cm$^{-1}$ NMR (CDCl$_3$):
$\delta$1.6 – 2.7m (2H), 3.02t (2H, J = 7 cps) 3.42s (6H), 4.49t (1H, J = 5 cps), 5.61 broad (2H), 7.08s (4H), 7.38 A$_2$B$_{2q}$ (4H)

| Analyzed as C$_{19}$H$_{21}$NO$_3$S$_2$Cl$_2$: | C | H | S |
|---|---|---|---|
| Calculated: | 51.12 | 4.74 | 14.37 |
| Found: | 51.19 | 4.69 | 14.41 |

EXAMPLE A-16

5.00 Grams of isopropyl isopropylthiomethyl sulfoxide was dissolved in 70 ml of anhydrous THF, and to which 675 mg of sodium hydride was added under cooling with ice, followed by an hour's stirring at 0° C.

and another hour's stirring at room temperature. The reaction mixture was again placed on ice water, and into which 5.42 ml of 4,4-dimethoxybutyronitrile was dropped, followed by 11.5 hours' stirring at room temperature and hours' stirring at 50° C., addition of 50 ml of methylene chloride and 1 ml of water, and by 30 minutes' stirring at 0° C. and an hour's stirring at room temperature. The reaction mixture was dried with Glauber's salt, and filtered. The filtrate was concentrated under reduced pressure. Subjecting the residue to a column chromatography (silica gel, methylene chloride, ethyl acetate, 10% methanol-ethyl acetate, and methanol), 1.66 g of 1-isopropylsulfinyl-1-isopropylthio-2 -amino-5,5-dimethoxy-1-pentene was parted as a light yellow, oily substance. The yield was 19%.

IR (neat): 3130, 3175, 3275, 3420, 1007 cm$^{-1}$

NMR (CDCl$_3$):

$\delta$0.86d (3H, J = 7Hz); 1.20d (3H, J = 7Hz), 1.25d (3H, J = 7Hz), 1.38d (3H, J = 7Hz), 1.54 – 2.18m (2H), 2.36 – 2.93m (2H), 2.98 – 3.72m (2H), 3.33s (6H), 4.35t (1H, J = 5Hz), 5.50 broad (1H)

EXAMPLE A-17

2.370 Grams of methyl methylthiomethyl sulfoxide was dissolved in 20 ml of anhydrous THF, and to which 475 mg of sodium hydride was added under cooling with ice, followed by 50 minutes' stirring at 0° C. and additional 50 minutes' stirring at room temperature. Again ice-cooling the system 3.73 ml of 4,4-dimethoxybutyronitrile was added dropwise, followed by 18 hours' stirring and further 23 hours' stirring at 50° – 55° C. The reaction liquid was again cooled with ice while 30 ml of methylene chloride and 1 ml of water were added thereto, and after a little while the temperature was returned to the normal level, followed by 3 hours' stirring. After an overnight's drying with Glauber's salt, the reaction mixture was filtered, and the solvent was evaporated off under reduced pressure. The residue was parted by a column chromatography (Florisil, methylene chloride, ethyl acetate and methanol), to allow the recovery of 457 mg of methyl methylthiomethyl sulfoxide and 4.332 g of a crystalline product. The crystals were dissolved in hot methylene chloride, and the insoluble matter was removed by filtration. The filtrate was concentrated under reduced pressure to leave 3.70 g of 1-methylsulfinyl-1-methylthio-2-amino-5,5-dimethoxy-1-pentene in light yellow, crystalline form. The yield was 76.5%, and the conversion yield was 94.8%. 1-Methylsulfinyl-1-methylthio-2-amino-5,5-dimethoxy-1-pentene (recrystallized from carbon tetrachloride): m.p. 86° – 87° C.

IR (KBr): 1008, 1627, 3150, 3273, 3400 cm$^{-1}$

NMR (CDCl$_3$):

Two types of geometrical isomers were present between E and Z.

o $\delta$2.29s (3H), 2.65s (3H), 3.37s (6H), 1.65 – 3.15m (4H) 4.40t (1H, J = 5.3Hz) 5.53 broad (2H)

o $\delta$2.19s (3H), 2.74s (3H), 3.37s (6H), 1.65 – 3.15m (4H), 4.45t (1H, J = 5.3Hz), 5.90 borad (2H)

| Analyzed as C$_9$H$_{19}$O$_3$S$_2$N: | C | H | S |
|---|---|---|---|
| Calculated: | 42.66 | 7.56 | 25.31 |
| Found: | 42.54 | 7.61 | 25.15 |

EXAMPLE A-18

1.20 Grams of methyl p-tolylthiomethyl sulfoxide was dissolved in 15 ml of THF, and added with 165 mg of sodium hydride under cooling with ice, followed by stirring for an hour at room temperature. Then 1 ml of benzonitrile was added to the solution, and stirred for 16.5 hours at room temperature and for 5 hours at 60° C., followed by addition of methylene chloride and 2 ml of water. After drying with Glauber's salt and filtration, the filtrate was concentrated under reduced pressure. The residue was washed with cyclohexane to obtain 1.212 g of 1-methylsulfinyl-1-(p-tolylthio)-2-amino-2-phenylethylene.

Colorless crystals, m.p. 171° – 172° C. (dec)

IR (KBr):
3400, 3240, 3105, 1620, 1517, 1493, 1008 cm$^{-1}$

NMR (CDCl$_3$):

$\delta$2.30s (3H), 2.44s (3H), 5.40 broad (2H), 7.17 A$_2$B$_{2q}$ (4H, J = 8Hz), 7.43s (5H)

EXAMPLE A-19

995 Milligrams of methyl methylthiomethyl sulfoxide was dissolved in 10 ml of THF, and to the solution 235 mg of sodium hydride was added under cooling with ice, followed by stirring for 10 minutes. After 30 minutes' stirring at room temperature, the system was added with 1.4 ml of hydrocinnamonitrile, and stirred for 37.5 hours at room temperature and 9 hours at 55° C. Upon addition of 50 ml of methylene chloride and 2 ml of water, the system was stirred for 10 minutes at room temperature, followed by drying with Glauber's salt and filtration. The filtrate was concentrated under reduced pressure. The residue was subjected to a column chromatography (silica gel, methylene chloride, ethyl acetate, and methanol) to separate 1.515 g of 1-methylsulfinyl-1-methylthio-2-amino-4-phenyl-1-butene. The yield was 74%.

Colorless crystals, m.p. 119° – 121° C. (from CH$_2$Cl$_2$-CCl$_4$-C$_6$H$_{12}$)

IR (KBr): 3300, 3125, 1638, 1544, 997 cm$^{-1}$

NMR (CDCl$_3$):

$\delta$2.20s (3H), 2.27s (3H), 2.87m (4H), 5.57 broad (2H), 7.17s (5H)

(Signal of isomer of methyl appeared at 2.07 and 2.77)

| Analyzed as C$_{12}$H$_{17}$NOS$_2$: | C | H | S |
|---|---|---|---|
| Calculated: | 56.43 | 6.71 | 25.11 |
| Found: | 56.46 | 6.63 | 25.08 |

EXAMPLE B-1

To 361 mg of 1-methylsulfinyl-1-methylthio-2-amino-2-phenylethylene, 1 ml of conc. hydrochloric acid was added, and the system was allowed to stand at room temperature for 3.5 hours. Then 5 ml of ethanol and 20 ml of ether were added, and the precipitate was removed by filtration. The filtrate was concentrated under reduced pressure, and parted through a column chromatography (silica gel and n-hexane). Whereby 258 mg of methanethiol ester of phenylglyoxylic acid was obtained as a yellow, oily substance. The product was refined by reduced pressure distillation.

Phenylglyoxylic acid methanethiol ester: m.p. 40°–41° C. yellow crystals
IR (neat): 1673 cm$^{-1}$
NMR (CCl$_4$):
δ2.39s (3H), 7.2 – 7.65m (3H), 8.0 – 8.25m (2H)

EXAMPLE B-2

367 Milligrams of 1-methylsulfinyl-1-methylthio-2-amino-2-phenylethylene was dissolved in 5 ml of methylene chloride, and to which 1 ml of 10% diluted sulfuric acid was added, followed by 3.5 hours' stirring at room temperature. Further 30 ml of methylene chloride was added, and the reaction mixture was dried with Glauber's salt, and concentrated under reduced pressure. The residue was parted through a column chromatography [silica gel, and n-hexane-benzene mixture (1:1)], to give 168 mg of phenylglyoxylic acid methanethiol ester. The yield was 48.9%.

EXAMPLE B-3

144 Milligrams of 1-methylsulfinyl-1-methylthio-2-amino-2-phenylethylene was dissolved in 5 ml of methylene choride, added with 96 mg of cupric chloride, and stirred for 3 days at room temperature. Filtering the reaction mixture, the filtrate was concentrated under reduced pressure, and the residue was passed through a column chromatography (silica gel and benzene). Thus 106 mg of phenylglyoxylic acid methanethiol ester was parted as yellow crystals. The yield was 92.8%.

EXAMPLE B-4

10.00 Grams of 1-methylsulfinyl-1-methylthio-2-aminopropene was suspended in 30 ml of methylene chloride, and to which 10.32 g of cupric chloride dihydrate was added under ice-cooling, followed by 20 hours' stirring at room temperature. Whereupon a powdery precipitate was formed, which was removed by filtration. The filtrate was distilled under reduced pressure (82° – 89° C./70 – 80 mmHg), to allow the recovery of 7.35 g of a yellow liquid. Further refining the same by distillation, 4.59 g of pyruvic acid methanethiol ester boiling at 80° – 83° C./66 mmHg was obtained as a yellow liquid. The yield was 64.2%.
IR (neat): 1728, 1672 cm$^{-1}$
NMR (CDCl$_3$):
δ2.36s, 2.43s (relative intensity 1:1)

| Analyzed as C$_4$H$_6$O$_2$S: | C | H |
|---|---|---|
| Calculated: | 40.66 | 5.12 |
| Found: | 40.80 | 5.15 |

EXAMPLE B-5

5.709 Grams of 1-methylsulfinyl-1-methylthio-2-amino-3-methyl-1-butene was dissolved in 50 ml of methylene chloride, added with 5.30 g of cupric chloride dihydrate, and stirred for 22 hours at room temperature. The insoluble matter was removed by filtration, and the filtrate was distilled under reduced pressure to give 3.495 g of 2-oxo-3-methylbutyric acid methanethiol ester boiling at 72° – 73° C./19 mmHg, as a yellow oil. The yield was 81%.
IR (neat): 1720, 1670 cm$^{-1}$
NMR (CDCl$_3$):
δ1.13d (6H, J = 7H), 2.33s (3H), 3.36 septet (1H, J = 7Hz)

EXAMPLE B-6

11.002 Grams of 1-methylsulfinyl-1-methylthio-2-amino-5,5-dimethoxy-1-pentene was dissolved in 100 ml of methylene chloride, added with 7.43 of cupric chloride dihydrate, and stirred for 24.5 hours at room temperature. The insoluble white precipitate was moved by filtration, and the filtrate was reduced pressure distilled, allowing the recovery of 2-oxo-5,5-dimethoxyvaleric acid methanethiol ester boiling at 100° – 105° C./4 mmHg, in the form of a yellow oil.
IR (KBr): 1676, 1726 cm$^{-1}$
NMR (CDCl$_3$):
δ1.75 – 2.20m (2H), 2.36s (3H), 2.88t (2H, J = 7Hz) 3.33s (6H), 4.39t (1H, J = 5.5Hz)

EXAMPLE B-7

236 Milligrams of 1-methylsulfinyl-1-methylthio-2-amino-2-phenylethylene was dissolved in 10 ml of ethanol, added with 114 mg of cupric chloride (anhydride), and allowed to stand for 4 days at room temperature. Concentrating the system under reduced pressure, 30 ml of methylene chloride was added to the concentrate, and the insoluble matter was removed by filtration. The filtrate was again concentrated under reduced pressure, and parted through a column chromatography (Florisil and benzene). Thus 135 mg of phenylglyoxylic acid ethyl ester was obtained as a colorless liquid. The yield was 72.9%. The product was identified with the standard sample, by means of IR and NMR analyses.

EXAMPLE B-8

452 Milligrams of 1-methylsulfinyl-1-methylthio-2-aminopropene was dissolved in 5 ml of methanol, added with 369 mg of cupric chloride (anhydride), and stirred for 2 days at room temperature. Upon quantitative analysis with gas chromatography, it was confirmed that 243 mg of methyl pyruvate was formed. The yield was 82.0%. The product was isolated in the manner similar to Example B-7, and identified with the standard sample by means of IR and NMR analyses.

EXAMPLE B-9

375 Milligrams of 1-methylsulfinyl-1-methylthio-2-amino-3-methyl-1-butene was dissolved in 5 ml of methanol, added with 261 mg of cupric chloride (anhydride), and stirred for 2 days at room temperature. Through the post-treating procedures similar to those of Example B-7, 205 mg of isopropylglyoxylic acid methyl ester was obtained as a colorless liquid. The yield was 73.5%.

EXAMPLE B-10

339 Milligrams of 1-isopropylsulfinyl-1-isopropylthio-2-amino-3-phenylpropene was dissolved in 7 ml of ethanol, added with 154 mg of cupric chloride, and stirred for 2 days at room temperature. Subsequently treating the system similarly to Example B-7, 147 mg of phenylpyruvic acid ethyl ester was obtained. The yield was 67.2%.

EXAMPLE B-11

317 Milligrams of 1-methylsulfinyl-1-methylthio-2-amino-2-(3',4'-diethoxyphenyl)ethylene was dissolved in 5 ml of ethanol, added with 135 mg of cupric chloride, and stirred for 3 days at room temperature. Treating the system subsequently in the manner similar to Example B-7, 210 mg of (3,4-diethoxyphenyl)glyoxylic acid ethyl ester was obtained. The yield was 78.6%.

EXAMPLE C-1

To 1.72 g of 1-methylsulfinyl-1-methylthio-2-amino-3-methyl-1-butene, 5 ml of acetic anhydride and 5 ml of pyridine were added, and the system was stirred for 5 hours at room temperature. The excessive acetic anhydride and pyridine were removed under reduced pressure, and the residue was parted through a column chromatography (silica gel and methylene chloride). Thus 1.246 g of 2-acetylamino-2-methylthio-isovaleric acid methanethiol ester was obtained as light yellow crystals. The yield was 59.4%.

The analysis sample was the above product which was recrystallized from an ethanol-water system.

2-Acetylamino-2-methylthio-isovaleric acid methanethiol ester: m.p. 103° – 104° C. colorless crystals.
IR (KBr): 3330, 1680(sh), 1663, 1506 cm$^{-1}$
NMR (CDCl$_3$):
 $\delta$ 1.01d (3H, J = 6.5Hz), 1.12d (3H, J = 6.5Hz), 1.99s (3H), 2.09s (3H), 2.35s (3H), 2.88 septet (1H), 6.63 broad (1H)

| Analyzed as C$_9$H$_{17}$NO$_2$S$_2$: | C | H | S |
| --- | --- | --- | --- |
| Calculated: | 45.92 | 7.28 | 27.25 |
| Found: | 46.00 | 7.01 | 27.27 |

EXAMPLE C-2

To 383 mg of 1-methylsulfinyl-1-methylthio-2-amino-2-phenylethylene, 2 ml of acetic anhydride and 2 ml of pyridine were added, and the system was allowed to stand for 15 hours at room temperature. After removing the excessive acetic anhydride and pyridine by concentrating the system under reduced pressure, the concentrate was crystallized from a benzene-n-hexane system. Thus 263 ml of α-acetylamino-α-methylthiophenylacetic acid methanethiol ester was obtained as light yellow crystals.

The analytical sample was provided by recrystallizing the above from a carbon tetrachloride-n-hexane system and methanol.

α-Acetylamino-α-methylthiophenylacetic acid methanethiol ester: m.p. 174° – 174.5° C. colorless crystals
IR (KBr): 3230, 1690(sh), 1680(sh), 1655, 1520 cm$^{-1}$
NMR (CDCl$_3$):
 $\delta$ 2.05s (3H), 2.08s (3H), 2.25s (3H), 7.2 – 7.7m (6H)
Mass spectrum (100° C, 70 ev):
 m/e 222 (M-SCH$_3$, 14%), 194 (27%), 180 (24%), 174 (23%), 152 (41%), 146 (23%), 105 (88%), 77 (30%), 76 (11%), 51 (13%), 48 (27%), 47 (37%), 45 (19%), 43 (100%)

| Analyzed as C$_{12}$H$_{15}$NO$_2$S$_2$: | C | H | S |
| --- | --- | --- | --- |
| Calculated: | 53.50 | 5.61 | 23.81 |
| Found: | 53.44 | 5.44 | 23.88 |

EXAMPLE C-3

To 800 mg of 1-methylsulfinyl-1-methylthio-2-amino-2-phenylethylene, 2 ml of pyridine and 0.33 ml of acetic anhydride was added by the order stated. After 8 hours' standing at room temperature, the reaction mixture was concentrated under reduced pressure, and the residue was crystallized from carbon tetrachloride. Thus 603 mg of α-acetylamino-α-methylthiophenylacetic acid methanethiol ester was obtained. The yield was 63.6%.

EXAMPLE C-4

508 Milligrams of 1-methylsulfinyl-1-methylthio-2-amino-2-phenylethylene was suspended in 2.5 ml of 10% aqueous sodium hydroxide solution. Further 0.285 ml of benzoyl chloride was added to the suspension and well-mixed by shaking for 15 minutes at room temperature, followed by the addition of 50 ml of methylene chloride. After drying the reaction mixture with Glauber's salt, the residue of subsequent reduced pressure concentration was parted by a column chromatograhy [silica gel, benzene-n-hexane mixture (1:1), benzene, and methylene chloride]. Thus 174 ml of α-benzoylamino-α-methylthiophenylacetic acid methanethiol ester was obtained as light yellow crystals. The analytical sample was obtained by recrystallizing the above product from a methylene chloride-carbon tetrachloride system. The yield was 23.5%.

α-Benzoylamino-α-methylthiophenylacetic acid methanethiol ester: m.p. 157.5° – 159.5° C. colorless crystals
IR (KBr): 3330, 1657 1510, 1480 cm$^{-1}$
NMR (CDCl$_3$):
 $\delta$ 2.08s (3H), 2.29s (3H), 7.2 – 8.2m (11H)
Mass spectrum (70ev 100° C.):
 m/e 284 (10%), 256 (13%), 236 (12%), 105 (base peak), 104 (12%), 77 (38%), 51 (10%), 48 (9%), 47 (11%)

| Analyzed as C$_{17}$H$_{17}$NO$_2$S$_2$: | C | H | S |
| --- | --- | --- | --- |
| Calculated: | 61.60 | 5.17 | 19.35 |
| Found: | 61.51 | 5.09 | 19.32 |

EXAMPLE C-5

To 600 mg of 1-methylsulfinyl-1-methylthio-2-aminopropene, 2 ml of acetic anhydride and 2 ml of pyridine were added, and the system was allowed to stand for 18 hours at room temperature. Following a reduced pressure concentration, the residue was crystallized from a benzene-cyclohexane system. Thus 477 mg of 2-acetylamino-2-methylthiopropionic acid methanethiol ester was obtained as colorless crystals. The yield was 63.3%. The analytical sample was provided by recrystallizating the above product from a carbon tetrachloride-cyclohexane system.

2-Acetylamino-2-methylthiopropionic acid methanethiol ester: m.p. 122° – 123° C. colorless crystals
IR (KBr): 3250, 1685(sh), 1658, 1530 cm$^{-1}$ NMR (CDCl₃):
δ1.99s (3H), 2.02s (3H), 2.05s (3H), 2.36s (3H), 6.60 broad (1H)

Mass spectrum analysis (100° C 70ev):
m/e 207 (M⁺, trace), 160 (37%), 132 (64%), 118 (41%), 112 (11%), 90 (92%), 48 (11%), 47 (18%), 45 (13%), 43 (base peak), 42 (96%)

| Analyzed as C₇H₁₃NOS₂: | C | H | S |
|---|---|---|---|
| Calculated: | 40.55 | 6.32 | 30.94 |
| Found: | 40.28 | 6.13 | 31.01 |

EXAMPLE C-6

To 522 mg of 1-(p-tolyl)sulfinyl-1-methylthio-2-amino-2-phenyl ethylene, 2 ml of acetic anhydride and 2 ml of pyridine were added, and the system was allowed to stand for 20 hours at room temperature. Following the subsequent reduced pressure concentration, the concentrate was recrystallized from a carbon tetrachloride-n-hexane system. Thus 259 mg of α-acetylamino-α-(p-tolylthio)phenylacetic acid methanethiol ester was obtained as colorless crystals. m.p. 156° – 157° C.

IR (KBr): 3220, 1690(sh), 1680(sh), 1665 cm⁻¹
NMR (CDCl₃):
δ1.95s (3H), 2.23s (3H), 2.37s (3H), 6.85 broad (1H), 7.0 – 7.8m (9H)

EXAMPLE C-7

1.383 Grams of 1-methylsulfinyl 1-methylthio-2-amino-3-methyl-1-butene was dissolved in 10 ml of methylene chloride, and to which 1.5 ml of acetic anhydride and 1 ml of pyride were added, followed by 22 hours' stirring at room temperature. After the subsequent reduced pressure concentration, the residue was parted by a column chromatography (silica gel and methylene chloride). Thus 1.459 g of 2-acetylamino-2-methylthio-isovaleric acid methanethiol ester was obtained as light yellow crystals. The yield was 87%.

EXAMPLE C-8

627 Milligrams of 1-methylsulfinyl-1-methylthio-2-aminopropene was dissolved in 5 ml of methylene chloride, and to which 0.5 ml of acetic anhydride and 0.5 ml of pyridine were added. After 12 hours' stirring at room temperature, the reaction mixture was concentrated under reduced pressure, and the residue was parted through a column chromatography (silica gel and methylene chloride). Thus 684 ml of 2-acetylamino-2-methylthiopropionic acid methanethiol ester was obtained as colorless crystals. The yield was 87%.

EXAMPLE C-9

1.306 Grams of 1-methylsulfinyl-1-methylthio-2-amino-2-phenylethylene was suspended in 10 ml of acetic anhydride, and stirred for 5 days at room temperature. After removing the excessive acetic anhydride under a reduced pressure, the residue was parted through a column chromatography (silica gel and methylene chloride). Thus 1.365 g of α-acetylamino-α-methylthiophenylacetic acid methanethiol ester was obtained. The yield was 88%.

EXAMPLE C-10

2.439 Grams of 1-methylsulfinyl-1-methylthio-2-amino-2-phenylethylene was dissolved in 10 ml of methylene chloride, and to which 1.5 ml of acetic anhydride and 1 ml of pyridine were added, followed by 4 hours' stirring at room temperature. After removing the excessive methylene chloride by a reduced pressure concentration, 10 ml of water was added to the residue, and the precipitated crystals were recovered by filtration. Thus 2.593 g of α-acetylamino-α-methylthiophenylacetic acid methanethiol ester was obtained. The yield was 88%.

EXAMPLE C-11

To 300 mg of 1-methylsulfinyl-1-methylthio-2-amino-5,5-dimethoxy-1-pentene, 1 ml of acetic anhydride was added. After 16 hours' standing at room temperature, the acetic anhydride and acetic acid were removed from the system under a reduced pressure, leaving a crystalline product. Recrystallizing said product from a carbon tetrachloride-cyclohexane-benzene system, 229 mg of 2-acetylamino-2-methylthio-5,5-dimethoxyvaleric acid methanethiol ester was obtained. Subjecting the mother liquor to a column chromatography (Florisil, methylene chloride, ethyl acetate, and methanol) 25 mg of 2-acetylamino-2-methylthio-5,5-dimethoxyvaleric acid methanethiol ester was parted. The yield was 72.7%.

2-Acetylamino-2-methylthio-5,5-dimethoxyvaleric acid methanethiol ester: m.p. 101° – 102° C. colorless crystals IR (KBr): 1668 – 1692, 3272 cm⁻¹
NMR (CDCl₃):
δ1.96s (3H), 2.07s (3H), 2.38s (3H), 1.2 – 2.3m (4H), 3.32s (6H), 4.37t (1H, J = 5.6Hz) 6.72 broad (1H)

| Analyzed as C₁₁H₂₁O₄NS₂: | C | H | S |
|---|---|---|---|
| Calculated: | 44.72 | 7.17 | 21.71 |
| Found: | 44.46 | 6.88 | 21.64 |

EXAMPLE D-1

To 243 mg of methanethiol ester of 2-acetylamino-2-methylthiopropionic acid, 2.3 cc of Raney nickel (WII) was added together with 7 ml of ethanol, and stirred for an hour at room temperature. The insoluble matter was removed by filtration, and the filtrate was concentrated under reduced pressure. The residue was passed through a column chromatography (silica gel, ethyl acetate and methylene chloride), to give 66 mg of an ethyl ester of N-acetylalanine. The yield was 35.4%. The product was identified with the standard sample by means of IR and NMR analyses.

EXAMPLE D-2

285 Milligrams of 2-acetylamino-2-methylthio-isovaleric acid methanethiol ester was dissolved in 5 ml of ethanol, and to the solution 2.2 cc of Raney nickel (WII) was added together with 8 ml of ethanol. After stirring for 1.5 hours at room temperature, the system was filtered. The filtrate was concentrated under a reduced pressure, and the residue was parted by a column chromatography (silica gel and ethyl acetate). Thus 137 mg of an ethyl ester of N-acetylvaline was obtained. The yield was 60.4%. The product was identified with the standard sample by means of IR and NMR analyses.

EXAMPLE D-3

308 Milligrams of α-acetamino-α-methylthiophenylacetic acid methanethiol ester was dissolved in 5 ml of ethanol, and to the solution 2.1 cc of Raney nickel (WII) was added together with 15 ml of ethanol. After an hour's stirring at room temperature, the system was filtered to be removed of the insoluble matter. The filtrate was concentrated under reduced pressure, and parted through a column chromatography (silica gel and ethyl acetate). Thus 96 mg of a colorless oil was obtained, which was confirmed to be a 3:4 mixture of N-acetylphenylglycine ethyl ester and N-benzylacetamide, by NMR quantitative analysis. The yield of N-acetylphenylglycine ethyl ester was 12%.

EXAMPLE D-4

Into an ethanol solution containing 1.5 cc of Raney nickel, 200 mg of 2-acetylamino-2-methylthio-5,5-dimethoxyvaleric acid methanethiol ester was added, and stirred at 0° C. for 2 hours. The insoluble matter was removed by filtration, and the filtrate was concentrated under reduced pressure. The residue was parted through a column chromatography (silica gel, methylene chloride, 50% ethyl acetate-methylene chloride, and methanol), to provide 94.5 mg of ethyl 2-acetylamino-5,5-dimethoxyvalerate as a colorless oil. The yield was 56.4%.

Properties of the colorless oil:
IR: 1651, 1738, 3270 cm$^{-1}$
NMR (CdCl$_3$):
  δ1.28t (3H, J = 7.5Hz), 1.5 – 2.0m (4H), 2.03s (3H), 3.84s (6H), 4.11q (2H, J = 7Hz), 4.35t (1H, J = 5 cps) 4.4 – 4.8n (1H), 5.9 – 6.4 borad (1H)

EXAMPLE D-5

To a suspension formed of 1.5 cc of Raney nickel (WII) suspended in 15 ml of ethanol, 360 mg of β-(5-benzyloxyindolyl-3)-α-acetylamino-α-methylthiopropionic acid methanethiol ester was added, and stirred for 1.5 hours at room temperature. Then the reaction mixture was filtered, and the separated solid was washed with ethanol. The filtrate and washing were combined and concentrated under reduced pressure, and the residue was parted through a column chromatography (silica gel, 10% ethyl acetate-methylene chloride, and ethyl acetate). Thus 105 mg of ethyl α-(5-benzyloxyindolyl-3)-α-acetylaminopropionate was obtained as a colorless oil. The yield was 32%.

Properties of the colorless oil:
IR (neat): 3400 – 3270, 1735, 1655 cm$^{-1}$
NMR (CDCl$_3$):
  δ 1.21t (3H, J = 7.2Hz), 1.92s (3H), 3.28d (2H, J = 5.5Hz), 4.15q (2H, J = 7.2Hz), 5.00m (1H), 5.10s (2H), 6.08 broad d (1H, NH), 6.8 – 7.3m (9H), 8.23 broad s (1H, NH)

EXAMPLE D-6

To 10 ml of acetone, 2.6 cc of Raney nickel (WII) was added, and the system was heated under reflux for 8 minutes. Then 314 mg of 2-acetylamino-2-methylthiopropionic acid methanethiol ester was added at room temperature, and stirred for 5 hours. The insoluble matter was removed by filtration, and the filtrate was concentrated under reduced pressure. Subjecting the concentrate to a column chromatography (silica gel and ethyl acetate), 182 mg of N-acetylalanine methanethiol ester was obtained. The yield was 74.5%.

N-acetylalanine methanethiol ester: m.p. 53° – 54.5° C. colorless crystals
IR (KBr): 3290, 1690(sh), 1680(sh), 1650, 1550 cm$^{-1}$
NMR (CDCl$_3$):
  δ1.37d (3H, J = 8Hz), 2.03s (3H), 2.26s (3H), 4.60 quintet (1H, J = 8Hz), 7.06 broad (1H)

| Analyzed as $C_6H_{11}NO_2S$: | C | H | S |
|---|---|---|---|
| Calculated: | 44.70 | 6.88 | 19.89 |
| Found: | 44.89 | 7.05 | 19.85 |

EXAMPLE D-7

To 10 ml of acetone, 1.8 cc of Raney nickel (WII) was added, and heated under reflux for 5 minutes. Cooling the system to room temperature, 250 mg of the methanethiol ester of α-acetylamino-α-methylthiophenylacetic acid was added, followed by 4 hours' stirring at room temperature. The insoluble matter was removed by filtration, and the filtrate was concentrated under reduced pressure and parted by a column chromatography (silica gel and ethyl acetate). Thus 157 mg of methanethiol ester of N-acetylphenylglycine was obtained as colorless crystals.

N-acetylphenylglycine methanethiol ester: m.p. 82°–84° C.
IR (KBr): 3225, 1680, 1640, 1515 cm$^{-1}$
NMR (CDCl$_3$):
  δ 1.98s (3H), 2.27s (3H), 5.72d (1H, J = 7Hz), 7.37s (5H), 7.30 broad (1H)

| Analyzed as $C_{11}H_{13}NO_2S$: | C | H | S |
|---|---|---|---|
| Calculated: | 59.17 | 5.87 | 14.36 |
| Found: | 59.23 | 5.64 | 13.95 |

EXAMPLE D-8

A suspension formed of 2.6 cc of Raney nickel (WII) suspended in 10 ml of acetone was heated under reflux for 8 minutes, and cooled to room temperature. Then 274 mg of a methanethiol ester of 2-acetylamino-2-methylthioisovaleric acid was added, and the system was stirred for 4 hours at room temperature. The insoluble matter was removed by filtration, and the filtrate was concentrated under reduced pressure. The concentrate was parted by a column chromatography (silica gel, methylene chloride and ethyl acetate). Thus 180 mg of a methanethiol ester of N-acetylvaline was obtained as colorless crystals. The yield was 82.7%.

N-acetylvaline methanethiol ester (recrystallized from a benzene-n-hexane system): m.p. 77.5°–78.5° C.
IR (KBr): 3275, 1690(sh), 1680(sh), 1650, 1530 cm$^{-1}$
NMR (CDCl$_3$):
  δ0.86d (3H, J = 7Hz), 0.97 (3H, J = 7Hz), 2.10s (3H), 2.29s (3H), 2.0 – 2.3 (1H), 4.47d of d (1H, J = 5.3, 9.5Hz), 6.75 broad (1H)

| Analyzed as $C_8H_{15}NO_2S$: | C | H | S |
|---|---|---|---|
| Calculated: | 50.76 | 7.99 | 16.94 |
| Found: | 50.84 | 8.25 | 16.93 |

EXAMPLE D-9

Example D-6 was repeated except that the Raney nickel was replaced by 2.5 cc of Urushibara nickel. Whereby 163 mg of N-acetylalanine methanethiol ester was obtained. The yield was 67%.

EXAMPLE D-10

To a mixture of 1.7 cc of Raney nickel (WII) and 5 ml of ethanol, 0.1 ml of conc. hydrochloric acid was added, and stirred for 5 minutes at room temperature. Then 183 mg of $\alpha$-acetylamino-$\alpha$-methylthiophenylacetic acid methanethiol ester was added, and stirred for 30 minutes at room temperature. After removing the insoluble matter by filtration, the filtrate was concentrated under reduced pressure. The concentrate was parted by a column chromatography (silica gel and ethyl acetate), to provide 85 mg of the methanethiol ester of N-acetylphenylglycine. The yield was 55.7%.

EXAMPLE D-11

Deactivated Raney nickel was formed by suspending 3.10 cc of Raney Ni in 15 ml of acetone, and refluxing the suspension for 5 minutes. Cooling the system to room temperature, 220 mg of 2-acetylamino-2-methylthio-5,5-dimethoxyvaleric acid methanethiol ester was added, followed by 4.5 hours' stirring at room temperature. The insoluble matter was removed by filtration, and the filtrate was concentrated under a reduced pressure. The residue was parted by a column chromatography (silica gel, methylene chloride, and ethyl acetate), to provide 127 mg of 2-acetylamino-5,5-dimethoxyvaleric acid methanethiol ester as a colorless oil. The yield was 68.3%.

Properties of the colorless oil:
IR: 1660, 1688, 3273 cm$^{-1}$
NMR (CDC$_3$):
$\delta$2.05s (3H), 2.80s (3H), 1.5 – 2.1m (4H), 3.35s (6H) 4.36t (1H, J = 5 cps), 4.4 – 4.9m (1H), 6.4 – 6.9m (1H)

EXAMPLE D-12

Deactivated Raney nickel was formed by suspending 1.2 cc of Raney Ni (WII) in 10 ml of acetone, and heating the suspension under reflux for 10 minutes. Cooling the system to room temperature, 254 mg of a methanethiol ester of $\beta$-(5-benzyloxyindolyl-3)-$\alpha$-acetylamino-$\alpha$-methylthiopropionic acid was added, followed by 4 hours' stirring. The insoluble matter was separated by filtration, and washed with acetone. The filtrate and washing were combined and concentrated under reduced pressure. The residue was washed with a 1:1 mixed solvent of ether and n-hexane. The remaining 110 mg of a colorless solid was identified to be the methanethiol ester of $\beta$-(5-benzyloxyindolyl-3)-$\alpha$-acetylamino-$\alpha$-methylthiopropionic acid, by IR analysis. The washing was also concentrated under reduced pressure, and parted by a column chromatography (silica gel, methylene chloride and ethyl acetate) to provide 77 mg of a light yellow, glassy substance. From the physical data given below, the substance was concluded to be $\beta$-(5-benzyloxyindolyl-3)-$\alpha$-acetylaminopropionic acid methanethiol ester. The yield was 34%, and the conversion was 60%.

IR (KBr): 1660, 1690, 3250 — 3380 cm$^{-1}$
NMR (CDCl$_3$):
$\delta$1.93s (3H), 2.23s (3H), 3.28d (2H, J = 6Hz), 4.8 – 5.3m (1H), 5.21s (2H), 5.8 – 6.2 broad d (1H), 6.7 – 7.7m (9H), 8.1 – 8.4 broad (1H)

EXAMPLE E-1

To 205 mg of methyl $\beta$-(5-benzyloxyindolyl-3)-$\alpha$-acetylamino-$\alpha$-methylthiopropionate, 2.0 cc of a deactivated Raney nickel, which had been formed by refluxing Raney Ni (WII) together with 10 ml of acetone for 10 minutes, and 15 ml of acetone were added, and stirred for 4.5 hours at room temperature. The insoluble matter was separated by filtration and washed with 50 ml of ethanol. The filtrate and washing were combined, concentrated under reduced pressure, and parted by a column chromatography [silica gel, and 1:19 mixture of ethyl acetate and methylene chloride]. Thus 102 mg of methyl $\beta$-(5-benzyloxyindolyl-3)-$\alpha$-acetylaminopropionate was obtained. The yield was 56%.

EXAMPLE E-2

Four (4.0) cc of Raney nickel was suspended in 15 ml of acetone, and stirred for 2 hours at room temperature to be deactivated. To the system then 417 mg of 2-acetylamino-2-methylthio-5,5-dimethoxyvaleric acid methanethiol was added, followed by 18 hours' stirring at room temperature. After removing the insoluble matter by filtration, the filtrate was concentrated under reduced pressure. The residue was parted by a column chromatography (silica gel and ethyl acetate), to provide 310 mg of methyl 2-acetylamino-5,5-dimethoxyvalerate as a colorless oil. The yield was 89%.

NMR (CDCl$_3$):
$\delta$1.4 – 2.0m (4H), 2.02s (3H), 3.32s (6H), 3.75s (3H), 4.15 – 4.85m (2H), 6.30 broad (1H)
IR (neat): 1745, 1655 cm$^{-1}$

EXAMPLE E-3

To 192 mg of methyl $\alpha$-acetylamino-$\alpha$-methylthiophenylacetate, 2.00 cc of Raney nickel which had been deactivated by 7 minutes' refluxing with 15 ml of acetone was added, and stirred for 5.5 hours at room temperature. The insoluble matter was removed by filtration, and the filtrate was concentrated under reduced pressure. The residue was parted by column chromatography (silica gel and methylene chloride), to allow the recovery of 156 mg of methyl $\alpha$-acetylaminophenylacetate as colorless crystals.

EXAMPLE E-4

To 293 mg of a methyl ester of N-acetyl-$\alpha$-methylthiovaline, 2.6 cc of Raney nickel (WII) was added together with 15 ml of ethanol, and stirred for an hour at room temperature. The insoluble matter was separated by filtration, and washed with ethanol. The filtrate and the washing were combined and concentrated under reduced pressure. The residue was parted by column chromatography (silica gel and methylene chloride), to allow the recovery of 215 mg of a methyl ester of N-acetylvaline as a colorless oil. The yield was 93%.

EXAMPLE E-5

To 275 mg of an ethyl ester of N-acetyl-α-methylthioalanine, 2.1 cc of Urushibara nickel was added together with 15 ml of ethanol, and stirred for 2 hours at room temperature. The insoluble matter was separated by filtration, and washed with ethanol. The filtrate and washing were combined, and concentrated under reduced pressure. Subjecting the residue to a column chromatography (silica gel and methylene chloride), 206 mg of an ethyl ester of N-acetylalanine was obtained. The yield was 90%.

EXAMPLE E-6

Two (2.0) cc of Raney nickel (WII) was suspended in 15 ml of acetone, and refluxed for 7 minutes. Cooling the suspension to room temperature, 315 mg of α-acetylamino-α-tolylthiophenylacetic acid was added, followed by 5.5 hours' stirring at room temperature. The insoluble matter was separated by filtration, and washed with ethanol. The filtrate and washing were combined and concentrated under reduced pressure. The residue was crystallized from an ether-n-hexane system. Thus 141 mg of α-acetylaminophenylacetic acid was obtained. The yield was 73%.

EXAMPLE E-7

500 Milligrams of β-(5-benzyloxyindolyl-3)-α-acetylamino-α-methylthiopropionic acid was suspended in 30 ml of methanol, and into which ammonia gas was blown to the saturation point under stirring at room temperature. After the following 19 hours' stirring at room temperature, the reaction mixture was concentrated under reduced pressure. Parting the residue by a column chromatography (silica gel and ethyl acetate), 113 mg of methyl β-(5-benzyloxyindolyl-3)-α-acetylamino-α-methylthiopropionate was obtained. The yield was 23.5%.

EXAMPLE E-8

449 Milligrams of β-(5-benzyloxyindolyl-3)-α-acetylamino-α-methylthiopropionic acid methanethiol ester was added to 10 ml of methanol. After further addition of 1 ml of triethylamine, the system was refluxed for 17 hours. The reaction mixture was concentrated under reduced pressure, and the residue was parted by a column chromatography (silica gel and ethyl acetate). Thus 353 mg of methyl β-(5-benzyloxyindolyl-3)-α-acetylamino-α-methylthiopropionate was obtained as a colorless, glassy substance. The yield was 81.5%. Recrystallizing the same from a methanol-water system, 287 mg of colorless crystals were obtained. The melting point was 178° – 179.5° C.

NMR (DMSO - $d_6$):
  δ1.85s (3H), 2.03s (3H), 3.32d (1H, J = 15 Hz), 3.71d (1H, J = 15Hz), 5.09s (2H), 6.7 – 7.6m (9H), 8.29s (1H, NH), 10.82 broad (1H, NH)

IR (KBr): 3360, 3200, 1736, 1600 cm$^{-1}$

| Analyzed as $C_{22}H_{24}O_4N_2S$: | C | H |
|---|---|---|
| Calculated: | 64.05 | 5.87 |
| Found: | 64.11 | 6.05 |

EXAMPLE E-9

2.2426 Grams of 2-acetylamino-2-methylthio-5,5-dimethoxyvaleric acid methanethiol ester was dissolved in 20 ml of methanol, and to which 2 ml of triethylamine was added, followed by 16.5 hours' refluxing. The reaction mixture was concentrated under reduced pressure, and the residue was parted by a column chromatography (florisil and methylene chloride). Thus 2.234 g of methyl 2-acetylamino-2-methylthio-5,5-dimethoxyvalerate was obtained. The yield was 97%.

NMR (CDCl$_3$):
  δ1.2 – 3.1m (4H), 2.04s (3H), 2.06s (3H), 3.32s (6H), 3.86s (3H), 4.37t (1H, J = 5.5Hz), 6.60 broad (1H)

IR (KBr): 3250, 1736, 1655 cm$^{-1}$

| Analyzed as $C_{11}H_{21}O_5NS$: | C | H | S |
|---|---|---|---|
| Calculated: | 47.29 | 7.58 | 11.48 |
| Found: | 47.12 | 7.40 | 11.50 |

EXAMPLE E-10

194 Milligrams of α-acetylamino-α-methylthiophenylacetic acid methanethiol ester was dissolved in 5 ml of methanol, and into which 2 drops of triethylamine was added, followed by 10.5 hours' refluxing. The reaction mixture was concentrated under reduced pressure, and the residue was parted by a column chromatography (silica gel and methylene chloride). Thus 158 mg of methyl α-acetylamino-α-methylthiophenylacetate was obtained as colorless crystals melting at 166° –167° C. The yield was 86%.

IR (KBr): 3200, 1737, 1650, 1530 cm$^{-1}$
NMR (CDCl$_3$):
  δ2.06s (6H), 3.75s (3H), 7.07 broad (1H), 7.17 – 7.74m (5H)

| Analyzed as $C_{12}H_{15}O_3SN$: | C | H | S |
|---|---|---|---|
| Calculated: | 56.89 | 5.97 | 12.66 |
| Found: | 56.89 | 5.88 | 12.77 |

EXAMPLE E-11

308 Milligrams of methanethiol ester of N-acetyl-α-methylthiovaline was dissolved in 10 ml of methanol, and to which 3 drops of triethylamine was added, followed by 15 hours' refluxing. The reaction mixture was concentrated under reduced pressure, and the residue was parted by a column chromatography [silica gel, and methylene chloride-ethyl acetate mixture (1:1)]. Thus 287 mg of a methyl ester of N-acetyl-α-methylthiovaline was obtained.

NMR (CDCl$_3$):
  δ1.00d (3H, J = 7.5 Hz), 1.13d (3H, J = 7.5Hz) 2.03s (3H), 2.10s (3H), 2.5 – 3.3m (1H), 3.87s (3H), 6.68 broad (1H)

IR (KBr): 1737, 1660, 3230 cm$^{-1}$

| Analyzed as $C_9H_{17}NO_3S$: | C | H |
|---|---|---|
| Calculated: | 49.29 | 7.81 |

-continued

| Analyzed as C₉H₁₇NO₃S: | C | H |
|---|---|---|
| Found: | 49.11 | 7.57 |

EXAMPLE E-12

1311 Milligrams of methanethiol ester of N-acetyl-α-methylthioalanine was dissolved in 10 ml of methanol, and to which 3 drops of triethylamine was added, followed by 15 hours' refluxing. Concentrating the reaction mixture under reduced pressure, the residue was parted by a column chromatography [silica gel, and methylene chloride-ethyl acetate mixture (1:1)]. Thus 262 mg of a methyl ester of N-acetyl-α-methylthioalanine was obtained. The yield was 91%.

NMR (CDCl₃):
 δ1.93s (3H), 2.07s (3H), 2.12s (3H), 3.85s (3H), 6.52 broad (1H)
IR (KBr): 3220, 1735, 1630 cm⁻¹

| Analyzed as C₇H₁₃NO₃S: | C | H |
|---|---|---|
| Calculated: | 43.97 | 6.85 |
| Found: | 43.94 | 6.88 |

EXAMPLE E-13

300 Milligrams of methanethiol ester of N-acetyl-α-methylthioalanine was dissolved in 10 ml of ethanol, and to which 3 drops of triethylamine was added, followed by 20.5 hours' refluxing. After a reduced pressure concentration of the reaction mixture, the residue was parted by a column chromatography (silica gel and methylene chloride). Thus 263 mg of an ethyl ester of N-acetyl-α-methylthioalanine melting at 70.5°–71.5° C. was obtained. The yield was 88%.

NMR (CDCl₃):
 δ1.29t (3H, J = 7Hz), 1.88s (3H), 2.02s (3H), 2.09s (3H), 4.23q (2H, J = 7Hz), 6.60 broad (1H)
IR (KBr): 1730, 1628, 1520 cm⁻¹

EXAMPLE E-14

Example E-12 was repeated except that the three drops of triethylamine was replaced by 5 drops of pyridine. Thus 235 mg of a methyl ester of N-acetyl-α-methylthioalanine was obtained. The yield was 82%.

EXAMPLE E-15

428 Milligrams of β--(5-benzyloxyindolyl-3)-α-acetylaminopropionic acid methanethiol ester and 276 mg of potassium carbonate were added to 10 ml of a methanol-water mixture (1:9), and refluxed for 3 hours. The reaction mixture was concentrated under reduced pressure to approximately 1 ml. The concentrate was diluted in 20 ml of water, which was acidified with 6-N hydrochloric acid. Extracting the system with methylene chloride and ethyl acetate, the organic phases were combined and dried with Glauber's salt. The residue was crystallized from a chloroformcarbon tetrachloride system, to provide 240 mg of β-(5-benzyloxyindolyl-3)-α-acetylaminopropionic acid melting at 166°–168.5° C. The yield was 63%.

EXAMPLE E-16

113 Milligrams of methyl α-acetylamino-α-methylthiophenylacetate and 41 mg of thiophenol were dissolved in 5 ml of methanol, and to the solution 0.5 ml of triethylamine was added, followed by an hour's refluxing. After a reduced pressure concentration of the reaction mixture, the residue was parted by a column chromatography (silice gel and methylene chloride). Thus 92 mg of methyl α-acetylaminophenylacetate was obtained. The yield was 99%.

EXAMPLE E-17

145 Milligrams of methyl α-acetylamino-α-methylthiophenylacetate was dissolved in 10 ml of methanol. To the solution 0.15 ml of triethyl phosphite was added, and the system was refluxed for 4.5 hours. Following a reduced pressure concentration, the residue was parted by a column chromatography (Florisil and methylene chloride) to provide 78 mg of methyl α-acetylaminophenylacetate. The yield was 65.5%.

EXAMPLE E-18

340 Milligrams of N-acetylamino-α-methylthiophenylacetic acid, 240 mg of isopropyl mercaptan, and 351 mg of potassium carbonate were added to 10 ml of a methanol-water mixture (9:1), and refluxed for 3 hours. Following a reduced pressure concentration of the reaction mixture to approximately 1 ml, 20 ml of water was added to the concentrate, which was then extracted with ethyl acetate. The organic phase was dried with Glauber's salt, and concentrated under reduced pressure. The residue was crystallized from an ether-n-hexane system, to provide 247 mg of α-acetylaminophenylacetic acid. The yield was 90%.

EXAMPLE E-19

173 Milligrams of a methanethiol ester of α-acetylamino-α-methylthiophenylacetic acid and 50 mg of thiophenol were dissolved in 10 ml of methanol. To the solution 1 ml of triethylamine was added, and the system was refluxed for 1.5 hours. Concentrating the reaction mixture under reduced pressure, the residue was parted by a column chromatography (silica gel and methylene chloride). Thus 127 mg of methyl α-acetylaminophenylacetate was obtained.

EXAMPLE E-20

368 Milligrams of α-acetylamino-α-methylthiophenylacetic acid methanethiol ester and 355 mg of potassium carbonate were added to 10 ml of a methanol-water mixture (9:1), and refluxed for 3 hours. The reaction mixture was concentrated under reduced pressure to approximately 1 ml. The concentrate was diluted with 20 ml of water, and extracted (methylene chloride 30 ml × 3 times, and ethyl acetate 30 ml × 3 times). The organic phases were collected, dried with Glauber's salt, and concentrated under reduced pressure. The residue was crystallized from an ether-n-hexane system to provide 241 mg of α-acetylaminophenylacetic acid. The yield was 91%.

EXAMPLE E-21

297 Milligrams of α-acetylamino-α-ethylthiophenylacetic acid ethanethiol ester and 0.2 ml of triethyl phosphite were dissolved in 10 ml of ethanol, and refluxed for 5 hours after the addition of 0.5 ml of triethylamine. Concentrating the reaction mixture under reduced pressure, the residue was parted by a column chromatography (Florisil and methylene chloride-ethyl acetate mixture). Thus 165 mg of ethyl α-acetylaminophynylacetate was obtained. The yield was 75%.

EXAMPLE E-22

353 Milligrams of α-acetylamino-α-butylthiophenyl acetic acid butanethiol ester was dissolved in 10 ml of propanol, and refluxed for 15 hours after a further addition of 0.3 ml of pyridine. Concentrating the reaction mixture under reduced pressure, the residue was parted by a column chromatography (silica gel, and a methylene chloride-ethyl acetate mixture). Thus 188 mg of propyl α-acetylaminophenyl acetate was obtained. The yield was 80%.

EXAMPLE E-23

Example E-20 was repeated except that 355 mg of potassium carbonate was replaced by 113 mg of sodium hydride. Thus 223 mg of α-acetylaminophenylacetic acid was obtained. The yield was 84%.

EXAMPLE E-24

387 Milligrams of α-acetylamino-α-methylthiophenylacetic acid methanethiol ester was dissolved in 5 ml of methanol. The solution was added with 0.5 ml of triethylamine and refluxed for 80 minutes. Concentrating the reaction mixture under reduced pressure, the residue was parted by a column chromatography (silica gel and methylene chloride). Thus 151 mg of methyl α-acetylaminophenylacetate was obtained. The yield was 51%.

We claim:
1. An enaminosulfoxide of the formula,

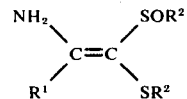

in which $R^1$ is alkyl, dialkoxyalkyl, phenylalkyl, phenyl, chlorophenyl, alkylphenyl, alkoxyphenyl or dialkoxyphenyl, said alkyl and alkoxy each containing 1 to 4 carbon atoms, and each $R^2$ is independently alkyl of 1 to 4 carbon atoms, phenyl, tolyl or chlorophenyl, wherein at least one of the $R^1$ and $R^2$ is aromatic.

2. An enaminosulfoxide of claim 1 wherein the enaminosulfoxide is 1-methylsulfinyl-1-methylthio-2-amino-2-phenylethylene.

3. An enaminosulfoxide of claim 1 wherein the enaminosulfoxide is 1-methysulfinyl-1-methylthio-2-amino-3-phenyl-1-propene.

4. An enaminosulfoxide of claim 1 wherein the enaminosulfoxide is 1-methylthio-1-(p-tolylsulfinyl)-2-amino-2-phenylethylene.

5. An enaminosulfoxide of claim 1 wherein the enaminosulfoxide is 1-(p-chlorophenyl)sulfinyl-1-(p-chlorophenyl)thio-2-amino,5,5-dimethoxy-1-pentene.

6. An enaminosulfoxide of claim 1 wherein the enaminoxulfoxide is 1-methylsulfinyl-1-methylthio-2-amino-2-(m-tolyl)ethylene.

7. An enaminosulfoxide of claim 1 wherein the enaminosulfoxide is 1-methylsulfinyl-1-(p-tolylthio)-2-amino-2-phenylethylene.

8. An enaminosulfoxide of claim 1 wherein the enaminosulfoxide is 1-methylsulfinyl-1-methylthio-2-amino-4-phenyl-1-butene.

9. An enaminosulfoxide of claim 1 wherein the enaminosulfoxide is 1-methylsulfinyl-1-methylthio-2-amino-2-(p-methoxyphenyl)ethylene.

10. An enaminosulfoxide of claim 1 wherein the enaminosulfoxide is 1-methylsulfinyl-1-methylthio-2-amino-2-(p-chlorophenyl)ethylene.

* * * * *